(12) United States Patent
Rajavenkatanarayanan et al.

(10) Patent No.: US 12,605,120 B2
(45) Date of Patent: Apr. 21, 2026

(54) SYSTEM FOR PREDICTING ONE OR MORE SPECIFIC COGNITIVE STATES BASED ON NON-NEURAL PHYSIOLOGICAL DATA

(71) Applicant: GM Global Technology Operations LLC, Detroit, MI (US)

(72) Inventors: Akilesh Rajavenkatanarayanan, Macomb, MI (US); Maureen Elizabeth August, Grosse Pointe Woods, MI (US); Brianna M. Duffy, La Jolla, CA (US); Mia Levy, Venice, CA (US); Andrew Howe, Malibu, CA (US); Rodolfo Valiente Romero, Calabasas, CA (US); Evelyn Kim, Irvine, CA (US)

(73) Assignee: GM GLOBAL TECHNOLOGY OPERATIONS LLC, Detroit, MI (US)

( * ) Notice: Subject to any disclaimer, the term of this patent is extended or adjusted under 35 U.S.C. 154(b) by 233 days.

(21) Appl. No.: 18/663,762

(22) Filed: May 14, 2024

(65) Prior Publication Data

US 2025/0352148 A1     Nov. 20, 2025

(51) Int. Cl.
A61B 5/16          (2006.01)
A61B 5/00          (2006.01)

(52) U.S. Cl.
CPC ............ A61B 5/7264 (2013.01); A61B 5/165 (2013.01)

(58) Field of Classification Search
None
See application file for complete search history.

(56) References Cited

U.S. PATENT DOCUMENTS

| | | | |
|---|---|---|---|
| 10,775,887 B2 | 9/2020 | Mohammadrezazadeh et al. | |
| 10,867,218 B2 * | 12/2020 | Gallagher ............. | G06F 18/256 |
| 2011/0118969 A1 * | 5/2011 | Krishnaswamy ...... | G01C 21/20 701/532 |
| 2013/0226408 A1 * | 8/2013 | Fung ........................ | A61B 5/18 701/1 |
| 2024/0132081 A1 | 4/2024 | Levy et al. | |

OTHER PUBLICATIONS

Notaro, G., et al. U.S. Appl. No. 18/425,277, filed Jan. 29, 2024.
Akbari et al., Semi-Recurrent Cnn-Based Vae-Gan for Sequential Data Generation, 2018 IEEE International Conference on Acoustics, Speech and Signal Processing (ICASSP), Apr. 1, 2018, p. 2321-2325, United States.

(Continued)

*Primary Examiner* — Abdhesh K Jha
(74) *Attorney, Agent, or Firm* — Vivacqua Crane, PLLC

(57)          ABSTRACT

A system for predicting one or more specific cognitive states of an individual based on non-neural physiological data collected by one or more non-neural physiological sensors includes one or more controllers in electronic communication with the one or more non-neural physiological sensors. The one or more controllers include a physiological data based neural network, a neural data based neural network, and an encoder-decoder that learns a transformation between a hidden layer of the physiological data based neural network and a hidden layer of the neural data based neural network during a training phase of the system.

17 Claims, 3 Drawing Sheets

(56)         References Cited

OTHER PUBLICATIONS

Gramfort et al., MEG and EEG data analysis with MNE-Python, Frontiers in Neuroscience, Dec. 26, 2013, vol. 7, Article 267, p. 1-13, Paris, France.

Babu et al., Multimodal approach for cognitive task performance prediction from body postures, facial expressions and EEG signal, Association for Computing Machinery, 2018, p. 1-7, vol. 14, https://doi.org/10.1145/3279810.3279849, United States.

Dao et al., An Attention Mechanism for Combination of CNN and VAE for Image-Based Malware Classification, IEEE Access, 2022, p. 85127-85136, vol. 10, 10.1109/Access.2022.3198072, United States.

Dedovic et al., The Montreal Imaging Stress Task: using functional imaging to investigate the effects of perceiving and processing psychosocial stress in the human brain, Journal of Psychiatry & Neuroscience: JPN, Sep. 30, 2005, p. 319-325, vol. 30, Issue 5. Montreal, Canada.

Hemakon et al., ECG and EEG based detection and multilevel classification of stress using machine learning for specified genders: A preliminary study, PLoS one, Sep. 1, 2023, p. 1-24, https://doi.org/10.1371/journal.pone.0291070, United States.

Iqbal et al., A Review of Biophysiological and Biochemical Indicators of Stress for Connected and Preventive Healthcare, Diagnostics (Basel), Mar. 19, 2021, p. 1-30, doi: 10.3390/diagnostics11030556, United States.

Jebelli et al., EEG-based workers' stress recognition at construction sites, Automation in Construction, 2018, p. 315-324, vol. 93, https://doi.org/10.1016/j.autcon.2018.05.027, United States.

Kim et al., Deep CNN transferred from VAE and GAN for classifying irritating noise in automobile, Neurocomputing, 2021, p. 395-403, vol. 452, https://doi.org/10.1016/j.neucom.2019.10.123., United States.

Lotfan et al., Support vector machine classification of brain states exposed to social stress test using EEG-based brain network measures, Biocybernetics and Biomedical Engineering, 2019, p. 199-213, vol. 39, Issue 1, https://doi.org/10.1016/j.bbe.2018.10.008., United States.

Lundberg et al., A Unified Approach to Interpreting Model Predictions, NIPS'17: Proceedings of the 31st International Conference on Neural Information Processing Systems, Dec. 2017, p. 4768-4777, United States.

Magal et al., Predicting Chronic Stress among Healthy Females Using Daily-Life Physiological and Lifestyle Features from Wearable Sensors, Chronic Stress (Thousand Oaks), Apr. 2022, p. 1-14, vol. 6, https://doi.org/10.1177/24705470221100987, United States.

Majid M. et al., Human stress classification using EEG signals in response to music tracks, Computers in Biology and Medicine, Apr. 2019, p. 182-196, vol. 107, https://doi.org/10.1016/j.compbiomed.2019.02.015, United States.

United States Patent and Trademark Office. U.S. Appl. No. 18/425,277, filed Jan. 29, 2024.

* cited by examiner

25 + 6 / (2+4) = ?

300

SYSTEM FOR PREDICTING ONE OR MORE SPECIFIC COGNITIVE STATES BASED ON NON-NEURAL PHYSIOLOGICAL DATA

INTRODUCTION

The present disclosure relates to a system for predicting one or more specific cognitive states of an individual based solely on non-neural physiological data, where the system is trained based on both the non-neural physiological data and neural data.

Direct neural data recorded from the human brain is the most reliable modality to detect the cognitive state of an individual. The most common and least invasive method of recording neural data is via electroencephalography (EEG). An EEG cap includes multiple electrodes that are affixed to the scalp of an individual that monitor the neural signals produced by the individual's brain. Another approach to detect the cognitive state of an individual relies upon sensors that monitor non-neural physiological data such as, but not limited to, heart rate, eye tracking, blood flow, and galvanic skin response. Current state-of-the-art approaches to detect the cognitive state of an individual may rely solely on neural data, solely on non-neural physiological data, or combinations thereof.

Although studies that only rely upon EEG data result in a relatively high level of accuracy when predicting the cognitive state and stress of an individual, EEG caps are invasive and are impractical for casual, everyday use by an individual. While collecting non-neural physiological data is less intrusive, studies that rely solely upon non-neural physiological data are often limited, may only be able to detect either extreme stress or no stress at all in an individual, and may lack the ability to obtain relatively high accuracy for more nuanced predictions. Studies that rely on both EEG and non-neural physiological data experience the same drawbacks as studies that only rely upon EEG data while also requiring additional physiological sensors, and only yield relatively minor improvements in performance when compared to studies that rely upon EEG data alone. There have been attempts to determine the transformation between non-neural physiological data and EEG data, however, these attempts have generally been unsuccessful.

Thus, while current approaches to detect the cognitive state of an individual achieve their intended purpose, there is a need in the art for an improved approach for determining the transformation between non-neural physiological data and EEG data.

SUMMARY

According to several aspects, a system for predicting one or more specific cognitive states of an individual based on non-neural physiological data collected by one or more non-neural physiological sensors is disclosed. The system includes one or more controllers in electronic communication with the one or more non-neural physiological sensors. The one or more controllers include one or more processors that execute instructions to receive, by a physiological data based neural network, the non-neural physiological data, where the physiological data based neural network is trained based on non-neural physiological training data collected by the one or more non-neural physiological sensors during a training phase of the system. In response to receiving the non-neural physiological data from the one or more non-neural physiological sensors, the physiological data based neural network predicts one or more intermediate specific cognitive states of the individual based on the non-neural physiological data. An encoder-decoder receives a hidden layer of the physiological data based neural network that is created as the physiological data based neural network predicts the one or more intermediate specific cognitive states of the individual. The encoder-decoder predicts a hidden layer of a neural data based neural network based on the hidden layer of the physiological data based neural network of the one or more intermediate specific cognitive states of the individual. The encoder-decoder transmits the hidden layer of the neural data based neural network to the neural data based neural network. The hidden layer of the neural data based neural network predicts the one or more specific cognitive states of the individual, where the neural data based neural network is trained based on neural training data, and the encoder-decoder learns a transformation between the hidden layer of the physiological data based neural network and the hidden layer of the neural data based neural network during the training phase of the system.

In an aspect, the one or more processors of the one or more controllers execute the training phase of the system by projecting, by one or more feedforward layers that are part of an encoder of the encoder-decoder, the hidden layer of the physiological data based neural network into latent space of the encoder-decoder to convert the hidden layer of the physiological data based neural network into a latent vector.

In another aspect, the one or more processors of the one or more controllers execute the training phase of the system by reconstructing, by one or more feedforward layers of a decoder of the encoder-decoder, the hidden layer of the neural data based neural network based on the latent vector.

In yet another aspect, the hidden layer of the physiological data based neural network matches the hidden layer of the neural data based neural network.

In an aspect, the neural training data is received from one or more electroencephalography (EEG) sensors worn by the individual during the training phase of the system.

In another aspect, the physiological data based neural network and the neural data based neural network are feed-forward neural networks.

In yet another aspect, the physiological data based neural network and the neural data based neural network are convolutional neural networks (CNN).

In an aspect, the encoder-decoder is a variational autoencoder (VAE).

In another aspect, the one or more processors of the one or more controllers execute a separate training phase for each unrelated cognitive state of the individual.

In yet another aspect, the one or more controllers of the system are in electronic communication with one or more controllers that are each part of one or more vehicle systems.

In an aspect, the one or more processors of the one or more controllers execute instructions to transmit the one or more specific cognitive states of the individual to the one or more controllers that are each part of the one or more vehicle systems, where the behavior of the one or more vehicle systems are modified based on the one or more specific cognitive states of the individual.

In another aspect, the one or more vehicle systems include one or more of the following: an audio system, an infotainment system, an automated driving system (ADS), an advanced driver assistance system (ADAS), and a navigation system.

In an aspect, a method for predicting one or more specific cognitive states of an individual based on non-neural physiological data collected by one or more non-neural physiological sensors is disclosed. The method includes receiving, by a physiological data based neural network of one or more controllers, the non-neural physiological data, where the physiological data based neural network is trained based on non-neural physiological training data collected by the one or more non-neural physiological sensors during a training phase of a system. In response to receiving the non-neural physiological data from the one or more non-neural physiological sensors, the method includes predicting, by the physiological data based neural network of the one or more controllers, one or more intermediate specific cognitive states of the individual based on the non-neural physiological data. The method includes receiving, by an encoder-decoder of the one or more controllers, a hidden layer of the physiological data based neural network that is created as the physiological data based neural network predicts the one or more intermediate specific cognitive states of the individual. The method includes predicting, by the encoder-decoder of the one or more controllers, a hidden layer of a neural data based neural network based on the hidden layer of the physiological data based neural network of the one or more intermediate specific cognitive states of the individual. The method also includes transmitting, by the encoder-decoder of the one or more controllers, the hidden layer of the neural data based neural network to the neural data based neural network. Finally, the method includes predicting, by the hidden layer of the neural data based neural network of the one or more controllers, the one or more specific cognitive states of the individual, where the neural data based neural network is trained based on neural training data, and where the encoder-decoder learns a transformation between the hidden layer of the physiological data based neural network and the hidden layer of the neural data based neural network during the training phase of the system.

In another aspect, the method includes transmitting, by the one or more controllers, the one or more specific cognitive states of the individual to the one or more controllers that are each part of one or more vehicle systems, where the behavior of the one or more vehicle systems are modified based on the one or more specific cognitive states of the individual.

In another aspect, a system for predicting one or more specific cognitive states of an individual based on non-neural physiological data is disclosed. The system includes one or more non-neural physiological sensors that each monitor a non-neural physiological measurement of the individual and one or more controllers in electronic communication with the one or more non-neural physiological sensors. The one or more controllers include one or more processors that execute instructions to receive, by a physiological data based neural network, the non-neural physiological data, where the physiological data based neural network is trained based on non-neural physiological training data collected by the one or more non-neural physiological sensors during a training phase of the system. In response to receiving the non-neural physiological data from the one or more non-neural physiological sensors, the one or more controllers predict, by the physiological data based neural network, one or more intermediate specific cognitive states of the individual based on the non-neural physiological data. An encoder-decoder receives a hidden layer of the physiological data based neural network that is created as the physiological data based neural network predicts the one or more intermediate specific cognitive states of the individual. The encoder-decoder predicts a hidden layer of a neural data based neural network based on the hidden layer of the physiological data based neural network of the one or more intermediate specific cognitive states of the individual. The encoder-decoder transmits the hidden layer of the neural data based neural network to the neural data based neural network. The hidden layer of the neural data based neural network predicts the one or more specific cognitive states of the individual, where the neural data based neural network is trained based on neural training data, and the encoder-decoder learns a transformation between the hidden layer of the physiological data based neural network and the hidden layer of the neural data based neural network during the training phase of the system.

In another aspect, the one or more processors of the one or more controllers execute the training phase of the system by projecting, by one or more feedforward layers that are part of an encoder of the encoder-decoder, the hidden layer of the physiological data based neural network into latent space of the encoder-decoder to convert the hidden layer of the physiological data based neural network into a latent vector.

In yet another aspect, the one or more processors of the one or more controllers execute the training phase of the system by reconstructing, by one or more feedforward layers of a decoder of the encoder-decoder, the hidden layer of the neural data based neural network based on the latent vector.

In an aspect, the hidden layer of the physiological data based neural network matches the hidden layer of the neural data based neural network.

In another aspect, the neural training data is received from one or more EEG sensors worn by the individual during the training phase of the system.

In yet another aspect, the one or more non-neural physiological sensors include one or more of the following: eye tracking sensors, thermal cameras for measuring blood flow in specific regions of the body of the individual, camera systems that record facial expressions and body pose of the individual, wearable sensors, and functional near-infrared spectroscopy (FNIRS) sensors.

Further areas of applicability will become apparent from the description provided herein. It should be understood that the description and specific examples are intended for purposes of illustration only and are not intended to limit the scope of the present disclosure.

BRIEF DESCRIPTION OF THE DRAWINGS

The drawings described herein are for illustration purposes only and are not intended to limit the scope of the present disclosure in any way.

DETAILED DESCRIPTION

The following description is merely exemplary in nature and is not intended to limit the present disclosure, application, or uses.

Figure 1:
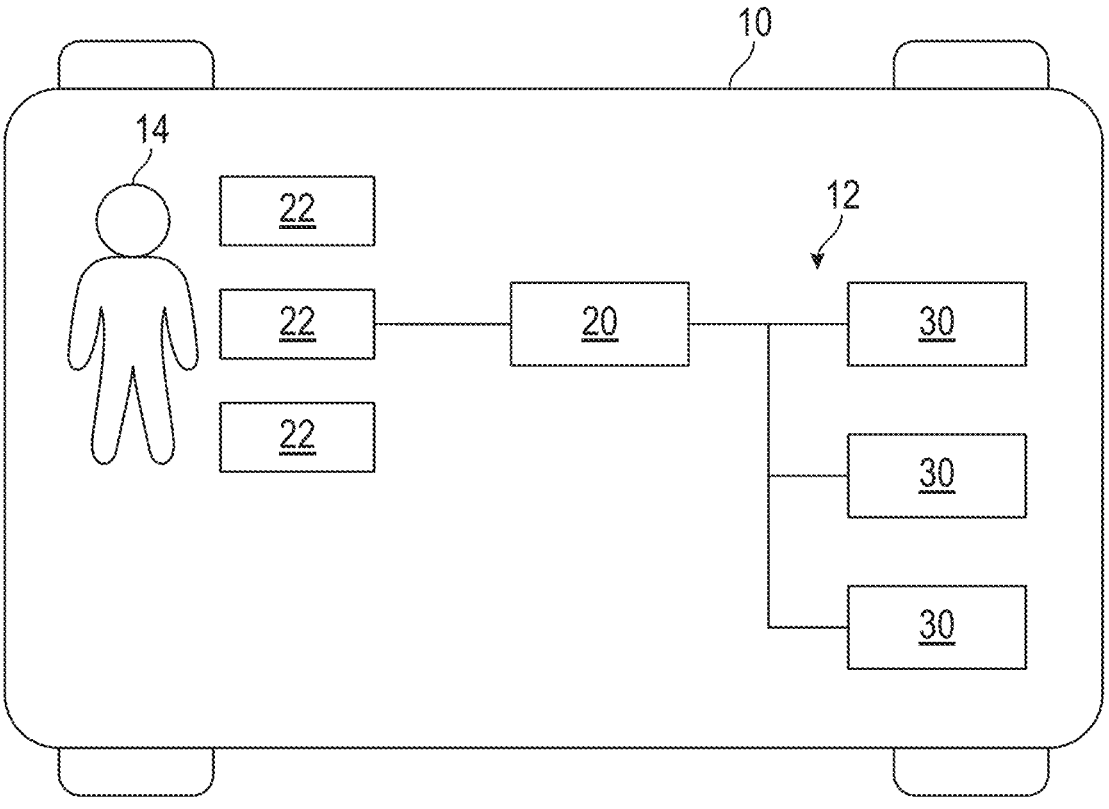
FIG. 1 is a schematic diagram of a vehicle including the disclosed system for predicting one or more specific cognitive states of an individual, where the system includes one or more controllers in electronic communication with one or more non-neural physiological sensors, according to an exemplary embodiment.

Referring to FIG. 1, a vehicle 10 including an exemplary system 12 for predicting one or more specific cognitive states of an individual 14 is illustrated. The system 12 includes one or more controllers 20 in electronic communication with one or more non-neural physiological sensors 22 that each monitor a non-neural physiological measurement of the individual 14. The one or more controllers 20 of the system 12 are also in electronic communication with one or more controllers 30 that are each part of one or more vehicle systems, where the behavior of the one or more vehicle systems are modified based on the predicted cognitive state of the individual 14. Some examples of vehicle systems that are modified based on the predicted cognitive state of the individual 14 include, but are not limited to, an audio system that plays music or other types of audio files, an infotainment system, an automated driving system (ADS), an advanced driver assistance system (ADAS), or a navigation system. Although FIG. 1 illustrates the system 12 as part of a vehicle, it is to be appreciated that the system 12 is not limited to a vehicle and may be used in a variety of other applications that consider the specific cognitive state of an individual. Merely by way of example, in another embodiment the system 12 is used to predict one or more specific cognitive states of an assembly line operator.

The non-neural physiological sensors 22 include any type of sensor for monitoring non-neural physiological data of the individual 14. In one non-limiting embodiment, the non-neural physiological sensors 22 include, but are not limited to, eye tracking sensors, thermal cameras for measuring the blood flow in specific regions of the body of the individual 14 and for respiration, camera systems that record facial expressions and body pose of the individual 14, wearable sensors, and functional near-infrared spectroscopy (FNIRS) sensors that measure non-neural physiological data such as respiration and the concentration of oxy-hemoglobin (O2Hb) and deoxy-hemoglobin (Hhb) in the prefrontal cortex of the individual 14. It is to be appreciated that the system 12 may include other types of non-neural physiological sensors 22 as well. For example, radar sensors may be used to detect respiration and heart rate, red, green, and blue (RGB) cameras may be used for remote heart rate sensing, accelerometers may be used to measure heart rate and breathing, and pressure sensors may be used to heart rate, body position, and respiration.

The wearable sensors are worn on the body of the individual 14 and measure non-neural physiological data such as, for example, pulse, heart rate variability, and galvanic skin response. The eye tracking sensors determine eye movement tracking such as, for example, a gaze position of the individual 14 in the x-direction and the y-direction, pupil dilation, eye distance, gaze velocity, and gaze acceleration. The thermal cameras determine the blood flow in regions of the face of the individual 14 such as, for example, the nose, nose tip, forehead, and left and right cheeks. The camera systems record facial expressions that indicate engagement, valence, and attention of the individual 14, and record facial expressions such as brow furrow, brow raise, inner brow raised, eye closure, eyes widening, cheek raise, and lip corner depressor.

Figure 2:
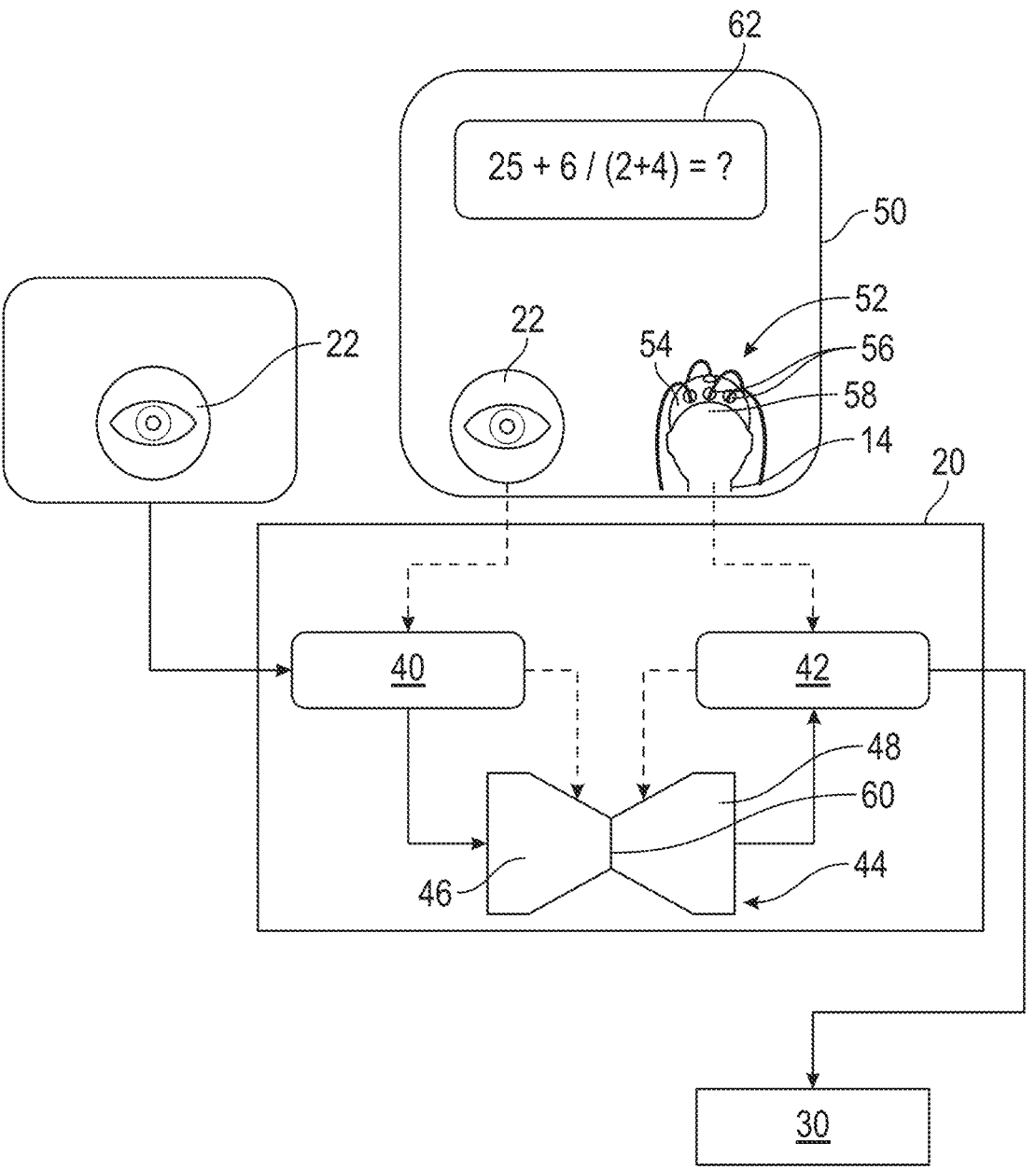
FIG. 2 is a block diagram illustrating the software architecture for the one or more controllers shown in FIG. 1, where the one or more controllers receive training data from neural sensors and the non-neural physiological sensors, according to an exemplary embodiment.

FIG. 2 is a block diagram illustrating the software architecture of the one or more controllers 20 of the system 12. The one or more controllers 20 include a physiological data based neural network 40, a neural data based neural network 42, and an encoder-decoder 44. In one non-limiting embodiment, the physiological data based neural network 40 and the neural data based neural network 42 are both convolutional neural networks (CNN), however, it is to be appreciated that any type of feed-forward neural network may be used instead such as, for example, a multilayer perceptron (MLP) neural network. In one embodiment the encoder-decoder 44 is a variational autoencoder (VAE), however, other types of encoder-decoders with generative capabilities such as a generative adversarial network (GAN) or another type of VAE may be used as well.

FIG. 2 illustrates both the physiological data based neural network 40 and the neural data based neural network 42 receiving training data 50 during a training phase of the system 12, where a dataflow of the training data is illustrated in dashed line. Specifically, the physiological data based neural network 40 receives non-neural physiological training data from the one or more non-neural physiological sensors 22 and the neural data based neural network 42 receives neural training data from one or more electroencephalography (EEG) sensors 52 worn by the individual 14. Specifically, in the embodiment as shown in FIG. 2, the EEG sensors 52 are an EEG cap 54 worn by the individual 14. The EEG cap 54 includes a plurality of electrodes 56 that are affixed to the scalp 58 of the individual 14.

It is to be appreciated that the physiological data based neural network 40 is trained based on non-neural physiological training data collected by the one or more non-neural physiological sensors 22 and the neural data based neural network 42 is trained based on neural training data from the one or more EEG sensors 52. As explained below, during a training phase of the system 12, both the physiological data based neural network 40 and the neural data based neural network 42 individually predict the one or more specific cognitive states of the individual 14 while the encoder-decoder 44 learns a transformation between a hidden layer of the physiological data based neural network 40 and a hidden layer of the neural data based neural network 42. During deployment, the system 12 only receives non-neural physiological training collected by the one or more non-neural physiological sensors 22 to predict the one or more specific cognitive states of the individual 14.

Determining the transformation between the hidden layer of the physiological data based neural network 40 and the hidden layer of the neural data based neural network 42 during the training phase of the system 12 shall now be described. It is to be appreciated that the encoder-decoder 44 may learn a transformation between any of the hidden layers of the physiological data based neural network 40 and any hidden layer of the neural data based neural network 42 during the training phase of the system 12. For example, the encoder-decoder 44 may learn the transformation between the final hidden layer of the physiological data based neural network 40 and the corresponding final hidden layer of the neural data based neural network 42 during the training phase of the system 12.

The encoder-decoder 44 includes an encoder 46, a decoder 48, and a latent space 60, where the latent space 60 is between the encoder 46 and the decoder 48. The encoder 46 of the encoder-decoder 44 includes one or more feedforward layers that project the hidden layer of the physiological data based neural network 40 into the latent space 60 to convert the hidden layer of the physiological data based neural network 40 into a latent vector. It is to be appreciated that the latent vector includes a smaller matrix dimension when compared to the matrix dimension of the hidden layer of the physiological data based neural network 40. Merely by way of example, in one embodiment the hidden layer of the physiological data based neural network 40 includes a matrix dimension of [1×2320] and the latent vector includes a matrix dimension of [1×100].

The latent vector includes a plurality of latent variables, where the matrix dimension of the latent vector indicates a total number of latent variables. In the current example, the latent vector has a matrix dimension of [1×100], which results in one hundred latent variables. Each latent variable of the latent vector is sampled from a probability distribution of possible values. In one non-limiting embodiment, the probability distribution is a normal distribution, however, it is to be appreciated that other types of probability distributions may be used as well. The decoder 48 of the encoder-decoder 44 receives the latent vector. The decoder 48 of the encoder-decoder 44 includes one or more feedforward layers that reconstruct the hidden layer of the neural data based neural network 42 based on the latent vector. It is to be appreciated that the hidden layer of the physiological data based neural network 40 matches the hidden layer of the neural data based neural network 42.

The system 12 is trained to predict one or more specific cognitive states of the individual 14, rather than all cognitive states that the individual 14 may be experiencing. In one embodiment, the one or more specific cognitive states of the individual 14 includes a subset of related cognitive states of the individual 14. The subset of related cognitive states represents cognitive states that result in similar physiological effects manifested by an individual. In the example as described, the subset of related cognitive states includes both stress and cognitive load of the individual 14. As another example, the subset of related cognitive states may include both excitement and fear, which both result in similar physiological effects such as high heart rate and a high level of alertness in an individual. In yet another example, the subset of related cognitive states may include both exhaustion and sadness. It is to be appreciated that the one or more specific cognitive states may include any other cognitive states manifested in the human body such as, for example, fear, joy, depression, and exhaustion. Furthermore, the one or more controllers 20 execute a separate training phase for unrelated cognitive states of the individual 14. For example, in the embodiment as described, another training phase is required to determine fear in the individual 14 once stress and cognitive load are predicted. It is to be appreciated that the system 12 focuses on predicting one or more specific cognitive states of the individual that are related to one another, rather than attempting to predict a variety of different, unrelated cognitive states, which simplifies and narrows the scope of the transformation learned by the encoder-decoder 44.

In one embodiment, the one or more specific cognitive states indicate either high stress or low stress and three distinct levels of cognitive load (low, medium, and high). The non-neural physiological training data and the neural training data are obtained by having the individual 14 complete three different sets of math problems 62 of increasing difficulty to simulate the three different levels of cognitive load. The math problems are solved in two different scenarios including a first, untimed scenario without external feedback that represents low stress conditions and a second, timed scenario where the individual 14 is given slightly less time than required during each of the three different sets of math problems and is constantly being given feedback comparing the individual's performance with his or her peers that represents high stress conditions.

Figure 3:
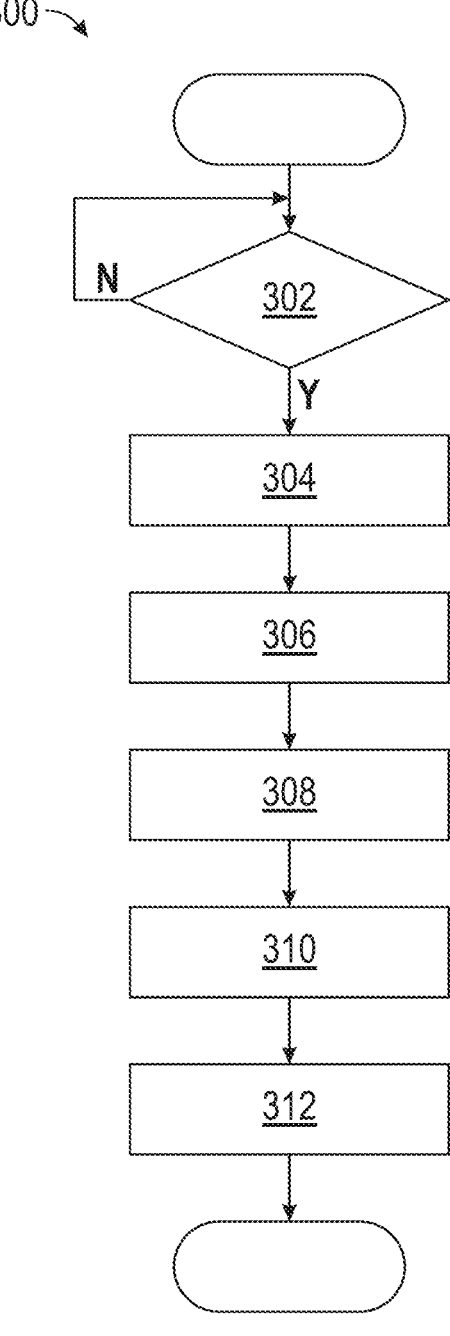
FIG. 3 is a process flow diagram illustrating a method for predicting one or more specific cognitive states of an individual based on non-neural physiological data collected by the non-neural physiological sensors, according to an exemplary embodiment.

Once the training phase is complete, the system 12 may predict the one or more specific cognitive states of the individual 14 during real-time operation based solely on the non-neural physiological training collected by the one or more non-neural physiological sensors 22. FIG. 3 is a process flow diagram illustrating a method 300 for predicting the one or more specific cognitive states of the individual 14. Referring to both FIGS. 2 and 3, the method 300 may begin at decision block 302. In decision block 302, the physiological data based neural network 40 of the one or more controllers 20 continues to monitor the one or more non-neural physiological sensors 22 until receiving the non-neural physiological data. As mentioned above, the physiological data based neural network is trained based on non-neural physiological training data collected by the one or more non-neural physiological sensors 22 during the training phase of the system 12. In response to receiving the non-neural physiological data, the method 300 may proceed to block 304.

In block 304, in response to receiving the non-neural physiological data from the one or more non-neural physiological sensors 22, the physiological data based neural network 40 of the one or more controllers 20 predicts one or more intermediate specific cognitive states of the individual 14 based on the non-neural physiological data. The method 300 may then proceed to block 306.

In block 306, the encoder-decoder 44 receives the hidden layer of the physiological data based neural network 40, where the hidden layer of the physiological data based neural network 40 is created as the physiological data based neural network 40 predicts the one or more intermediate specific cognitive states of the individual 14 based on the non-neural physiological data as described in block 304. The method 300 may then proceed to block 306.

In block 306, in response to receiving the hidden layer of the physiological data based neural network 40, the encoder-decoder 44 predicts the hidden layer of the neural data based neural network 42 based on the hidden layer of the physiological data based neural network 40 of the one or more intermediate specific cognitive states of the individual 14. The method 300 may then proceed to block 308.

In block 308, the encoder-decoder 44 transmits the hidden layer of the neural data based neural network 42 to the neural data based neural network 42. The method 300 may then proceed to block 310.

In block 310, the neural data based neural network 42 predicts the one or more specific cognitive states of the individual 14 based on the hidden layer of the neural data based neural network 42 received from the encoder-decoder 44. The method 300 may then proceed to block 312.

In block 312, the neural data based neural network 42 of the one or more controllers 20 transmits the one or more specific cognitive states of the individual 14 to the one or more controllers 30 that are each part of one or more vehicle systems. The behavior of the one or more vehicle systems are modified based on the one or more predicted cognitive states of the individual 14. The method 300 may then terminate.

Referring to FIG. 2, modifying the behavior of the one or more vehicle systems based on the one or more specific cognitive states of the individual 14 shall now be described. In one example, when the one or more specific cognitive states of the individual 14 indicates a high level of cognitive load and high stress, this indicates that the individual 14 may be driving the vehicle 10 under challenging conditions. Accordingly, the behavior of the one or more vehicle systems are modified to reduce driver distractions and notify various contacts of the individual 14. One example of a challenging condition is maneuvering the vehicle 10 down a steep mountain road during limited visibility conditions, such as rain or fog. In this example, the one or more controllers 30 corresponding to the audio system may turn off music so that the individual 14 may pay closer attention to the road, the controllers 30 corresponding to the infotainment system may notify the individual's emergency contact of the vehicle's location, and the one or more controllers 30 corresponding to the ADS or the ADAS may prompt the driver to take over control of the vehicle 10.

In another example, when the one or more specific cognitive states of the individual 14 indicates a medium level of cognitive load and high stress, this indicates the individual 14 is paying sufficient attention to driving conditions. Accordingly, the behavior of the one or more vehicle systems is modified based on the preferences of the individual 14. For example, if heavy traffic is delaying an estimated arrival time, then the one or more controllers 30 corresponding to the navigation system may ask the individual 14 if he or she is interested in taking an alternative route, the one or more controllers 30 corresponding to the infotainment system may text one of the individual's contacts to let them know the individual 14 may be late because of the delayed estimated arrival time, and the one or more controllers 30 corresponding to the audio system may reduce the volume of the audio being played.

In yet another example, when the one or more specific cognitive states of the individual indicates a low level of cognitive load and low stress, this indicates the individual 14 may be falling asleep. Accordingly, the one or more controllers 30 corresponding to the audio system may create a notification instructing the individual 14 to pay attention to the roads. Alternatively, when the one or more specific cognitive states of the individual indicates a low level of cognitive load and high stress, this indicates the individual 14 may be distracted and thinking about other issues (e.g., an ill family member in the hospital). Accordingly, the one or more controllers 30 corresponding to the audio system may play a favorite music playlist to soothe the individual 14.

Referring generally to the figures, the disclosed system for predicting the one or more specific cognitive states of an individual provides various technical effects and benefits. Specifically, the disclosed system provides an approach to learn the transformation between a hidden layer of the physiological data based neural network and a hidden layer of the neural data based neural network. Accordingly, the system may predict the one or more specific cognitive states of the individual during real-time operation based solely on non-neural physiological data, without utilizing invasive EEG sensors. It is to be appreciated that the disclosed system results in enhanced accuracy when compared to a system trained exclusively on non-neural physiological data. For example, in an embodiment, the disclosed system achieves an accuracy of about 87%. In contrast, a system trained using only non-neural physiological data achieves an accuracy of 76%. It is also to be appreciated that the physiological data based neural network preprocesses the non-neural physiological data before being sent to the encoder-decoder, which in turn denoises the non-neural physiological data and also narrows the objective of the encoder-decoder to focus only on task-relevant signals that are material to predicting the one or more specific cognitive states of the individual.

The controllers may refer to, or be part of an electronic circuit, a combinational logic circuit, a field programmable gate array (FPGA), a processor (shared, dedicated, or group) that executes code, or a combination of some or all of the above, such as in a system-on-chip. Additionally, the controllers may be microprocessor-based such as a computer having a at least one processor, memory (RAM and/or ROM), and associated input and output buses. The processor may operate under the control of an operating system that resides in memory. The operating system may manage computer resources so that computer program code embodied as one or more computer software applications, such as an application residing in memory, may have instructions executed by the processor. In an alternative embodiment, the processor may execute the application directly, in which case the operating system may be omitted.

The description of the present disclosure is merely exemplary in nature and variations that do not depart from the gist of the present disclosure are intended to be within the scope of the present disclosure. Such variations are not to be regarded as a departure from the spirit and scope of the present disclosure.

What is claimed is:

1. A system for predicting one or more specific cognitive states of an individual based on non-neural physiological data collected by one or more non-neural physiological sensors, the system comprising:

one or more controllers in electronic communication with the one or more non-neural physiological sensors, the one or more controllers including one or more processors that execute instructions to:

receive, by a physiological data based neural network, the non-neural physiological data, wherein the physiological data based neural network is trained based on non-neural physiological training data collected by the one or more non-neural physiological sensors during a training phase of the system;

in response to receiving the non-neural physiological data from the one or more non-neural physiological sensors, predict, by the physiological data based neural network, one or more intermediate specific cognitive states of the individual based on the non-neural physiological data;

receive, by an encoder-decoder, a hidden layer of the physiological data based neural network that is created as the physiological data based neural network predicts the one or more intermediate specific cognitive states of the individual;

predict, by the encoder-decoder, a hidden layer of a neural data based neural network based on the hidden layer of the physiological data based neural network of the one or more intermediate specific cognitive states of the individual;

transmit, by the encoder-decoder, the hidden layer of the neural data based neural network to the neural data based neural network; and predict, by the hidden layer of the neural data based neural network, the one or more specific cognitive states of the individual, wherein the neural data based neural network is trained based on neural training data, and wherein the encoder-decoder learns a transformation between the hidden layer of the physiological data based neural network and the hidden layer of the neural data based neural network during the training phase of the system, wherein the one or more controllers of the system are in electronic communication with one or more controllers that are each part of one or more vehicle systems, and wherein the one or more processors of the one or more controllers execute instructions to:

transmit the one or more specific cognitive states of the individual to the one or more controllers that are each part of the one or more vehicle systems, wherein the behavior of the one or more vehicle systems are modified based on the one or more specific cognitive states of the individual.

2. The system of claim 1, wherein the one or more processors of the one or more controllers execute the training phase of the system by:

projecting, by one or more feedforward layers that are part of an encoder of the encoder-decoder, the hidden layer of the physiological data based neural network into latent space of the encoder-decoder to convert the hidden layer of the physiological data based neural network into a latent vector.

3. The system of claim 2, wherein the one or more processors of the one or more controllers execute the training phase of the system by:

reconstructing, by one or more feedforward layers of a decoder of the encoder-decoder, the hidden layer of the neural data based neural network based on the latent vector.

4. The system of claim 1, wherein the hidden layer of the physiological data based neural network matches the hidden layer of the neural data based neural network.

5. The system of claim 1, wherein the neural training data is received from one or more electroencephalography (EEG) sensors worn by the individual during the training phase of the system.

6. The system of claim 1, wherein the physiological data based neural network and the neural data based neural network are feed-forward neural networks.

7. The system of claim 1, wherein the physiological data based neural network and the neural data based neural network are convolutional neural networks (CNN).

8. The system of claim 1, wherein the encoder-decoder is a variational autoencoder (VAE).

9. The system of claim 1, wherein the one or more processors of the one or more controllers execute a separate training phase for each unrelated cognitive state of the individual.

10. The system of claim 1, wherein the one or more vehicle systems include one or more of the following: an audio system, an infotainment system, an automated driving system (ADS), an advanced driver assistance system (ADAS), and a navigation system.

11. A method for predicting one or more specific cognitive states of an individual based on non-neural physiological data collected by one or more non-neural physiological sensors, the method comprising:

receiving, by a physiological data based neural network of one or more controllers, the non-neural physiological data, wherein the physiological data based neural network is trained based on non-neural physiological training data collected by the one or more non-neural physiological sensors during a training phase of a system;

in response to receiving the non-neural physiological data from the one or more non-neural physiological sensors, predicting, by the physiological data based neural network of the one or more controllers, one or more intermediate specific cognitive states of the individual based on the non-neural physiological data;

receiving, by an encoder-decoder of the one or more controllers, a hidden layer of the physiological data based neural network that is created as the physiological data based neural network predicts the one or more intermediate specific cognitive states of the individual;

predicting, by the encoder-decoder of the one or more controllers, a hidden layer of a neural data based neural network based on the hidden layer of the physiological data based neural network of the one or more intermediate specific cognitive states of the individual;

transmitting, by the encoder-decoder of the one or more controllers, the hidden layer of the neural data based neural network to the neural data based neural network;

predicting, by the hidden layer of the neural data based neural network of the one or more controllers, the one or more specific cognitive states of the individual, wherein the neural data based neural network is trained based on neural training data, and wherein the encoder-decoder learns a transformation between the hidden layer of the physiological data based neural network and the hidden layer of the neural data based neural network during the training phase of the system; and transmitting, by the one or more controllers, the one or more specific cognitive states of the individual to the one or more controllers that are each part of one or more vehicle systems, wherein the behavior of the one or more vehicle systems are modified based on the one or more specific cognitive states of the individual.

12. A system for predicting one or more specific cognitive states of an individual based on non-neural physiological data, the system comprising:

one or more non-neural physiological sensors that each monitor a non-neural physiological measurement of the individual; and one or more controllers in electronic communication with the one or more non-neural physiological sensors, the one or more controllers including one or more processors that execute instructions to:

receive, by a physiological data based neural network, the non-neural physiological data, wherein the physiological data based neural network is trained based on non-neural physiological training data collected by the one or more non-neural physiological sensors during a training phase of the system;

in response to receiving the non-neural physiological data from the one or more non-neural physiological sensors, predict, by the physiological data based neural network, one or more intermediate specific cognitive states of the individual based on the non-neural physiological data;

receive, by an encoder-decoder, a hidden layer of the physiological data based neural network that is created as the physiological data based neural network predicts the one or more intermediate specific cognitive states of the individual;

predict, by the encoder-decoder, a hidden layer of a neural data based neural network based on the hidden layer of the physiological data based neural network of the one or more intermediate specific cognitive states of the individual;

transmit, by the encoder-decoder, the hidden layer of the neural data based neural network to the neural data based neural network; and predict, by the hidden layer of the neural data based neural network, the one or more specific cognitive states of the individual, wherein the neural data based neural network is trained based on neural training data, and wherein the encoder-decoder learns a transformation between the hidden layer of the physiological data based neural network and the hidden layer of the neural data based neural network during the training phase of the system, wherein the one or more controllers of the system are in electronic communication with one or more controllers that are each part of one or more vehicle systems, and wherein the one or more processors of the one or more controllers execute instructions to:

transmit the one or more specific cognitive states of the individual to the one or more controllers that are each part of the one or more vehicle systems, wherein the behavior of the one or more vehicle systems are modified based on the one or more specific cognitive states of the individual.

13. The system of claim 12, wherein the one or more processors of the one or more controllers execute the training phase of the system by:

projecting, by one or more feedforward layers that are part of an encoder of the encoder-decoder, the hidden layer of the physiological data based neural network into latent space of the encoder-decoder to convert the hidden layer of the physiological data based neural network into a latent vector.

14. The system of claim 13, wherein the one or more processors of the one or more controllers execute the training phase of the system by:

reconstructing, by one or more feedforward layers of a decoder of the encoder-decoder, the hidden layer of the neural data based neural network based on the latent vector.

15. The system of claim 12, wherein the hidden layer of the physiological data based neural network matches the hidden layer of the neural data based neural network.

16. The system of claim 12, wherein the neural training data is received from one or more EEG sensors worn by the individual during the training phase of the system.

17. The system of claim 12, wherein the one or more non-neural physiological sensors include one or more of the following: eye tracking sensors, thermal cameras for measuring blood flow in specific regions of the body of the individual, camera systems that record facial expressions and body pose of the individual, wearable sensors, and functional near-infrared spectroscopy (FNIRS) sensors.

* * * * *